United States Patent [19]

Desbois

[11] Patent Number: 4,552,984

[45] Date of Patent: * Nov. 12, 1985

[54] PROCESS FOR PREPARATION OF α,α-DIFLUOROALKOXY OR α,α-DIFLUOROALKYLTHIOPHENYL SULFONES

[75] Inventor: Michel Desbois, Rillieux, France

[73] Assignee: Rhone-Poulenc Specialites Chimiques, Courbevoie, France

[*] Notice: The portion of the term of this patent subsequent to Nov. 19, 2002 has been disclaimed.

[21] Appl. No.: 392,884

[22] Filed: Jun. 28, 1982

[30] Foreign Application Priority Data

Jan. 21, 1982 [FR] France ............... 82 00878

[51] Int. Cl.$^4$ ........................................... C07C 149/34
[52] U.S. Cl. ................... 568/29; 260/465 F; 260/465 G; 562/429; 568/30; 568/31; 568/33
[58] Field of Search ............ 568/29, 33, 30, 31; 562/429; 260/465 F, 465 G

[56] References Cited

U.S. PATENT DOCUMENTS

| | | | |
|---|---|---|---|
| T970,006 | 5/1978 | Rose | 260/591 |
| 2,781,402 | 2/1957 | Chadwick | 568/34 |
| 2,974,172 | 3/1961 | Luvisi | 260/592 |
| 3,387,035 | 6/1968 | Gray et al. | 260/591 |
| 3,732,307 | 5/1973 | Middleton | 260/566 B |
| 3,883,594 | 5/1975 | Schmerling | 260/592 |
| 3,953,400 | 4/1976 | Dahl | 260/47 R |
| 3,967,949 | 7/1976 | Benefiel et al. | 71/76 |
| 3,970,752 | 7/1976 | Aichinger et al. | 424/249 |
| 4,178,460 | 12/1979 | Berkelhammer et al. | 562/426 |
| 4,207,266 | 6/1980 | Opie | 260/651 F |
| 4,276,226 | 6/1981 | Clement et al. | 260/410.5 |

FOREIGN PATENT DOCUMENTS

| | | |
|---|---|---|
| 43861 | 1/1981 | European Pat. Off. . |
| 0069598 | 1/1983 | European Pat. Off. . |
| 876690 | 5/1953 | Fed. Rep. of Germany . |
| 2451037 | 4/1976 | Fed. Rep. of Germany . |
| 1567806 | 4/1969 | France . |
| 2357517 | 2/1978 | France . |
| 54-135756 | 10/1979 | Japan . |
| 1164817 | 9/1969 | United Kingdom . |
| 2030158 | 4/1980 | United Kingdom . |
| 2045760 | 11/1980 | United Kingdom . |

OTHER PUBLICATIONS

Kirk-Othmer, *Encyclopedia of Chem. Technology*, vol. 13, p. 344 (1947).
Buu-Hoi et al., J. Org. Chem., vol. 26, 2401-2 (1961).
C. Hansch et al., J. Med. Chem., 1973, vol. 16, No. 11, p. 1207.
Chapman et al., *Correlation Analysis in Chemistry, Recent Advances*, Plenum Press (1978), p. 455.
G. Olah, Friedel-Crafts and Related Reactions, III, Part II, Chapter XL, (1964).
L. Yagupolskii et al., Chem. Abstracts, 61:8217 (1964).
V. Boiko et al., Chem. Abstracts 87:134226h (1977).
Yasui, K. et al., Chemical Abstract, 92:215144k (1980).
Morrison and Boyd, Organic Chemistry, p. 375 (1969), Allyn and Bacon, Inc. Boston.

*Primary Examiner*—Donald G. Daus
*Assistant Examiner*—Mary E. Ceperley
*Attorney, Agent, or Firm*—Schwartz, Herbert F.; James F. Haley, Jr.; Paul H. Ginsburg

[57] ABSTRACT

A process for the preparation of α,α-difluoroalkoxy or α,α-difluoroalkylthiophenyl sulfones, in which a polyhaloalkoxybenzene or a polyhaloalkylthiobenzene is reacted with a sulfonic acid, a derivative or a precursor of this acid, in the presence of boron trifluoride in an amount such that the absolute pressure of the boron trifluoride within the reaction vessel exceeds 1 bar, and in the presence of hydrofluoric acid as a solvent. The resultant products are useful as intermediates in the synthesis of compounds having a phytosanitary (e.g., herbicidal) or pharmaceutical activity.

8 Claims, No Drawings

PROCESS FOR PREPARATION OF α,α-DIFLUOROALKOXY OR α,α-DIFLUOROALKYLTHIOPHENYL SULFONES

The instant invention is directed to a process for the preparation of α,α-difluoroalkoxy or α,α-difluoroalkylthiophenyl sulfones.

Methods for the preparation of compounds of this type are already known in the art. For example, Chemical Abstracts 61-8217 describes the preparation of p-F$_3$COC$_6$H$_4$SO$_2$CF$_3$. According to the described process, paratrifluoromethoxyaniline obtained by nitration of trifluoromethoxybenzene is subjected to diazotization in an aqueous HCl medium. The resultant product is treated first with EtOCS$_2$K, then with potassium hydroxide, and finally with dimethyl sulfate to produce paratrifluoromethoxythioanisole. This product is chlorinated to give paratrifluoromethoxytrichloromethylthiobenzene. This compound is then treated with SbF$_3$ to produce paratrifluoromethoxytrifluoromethylthiobenzene, which is converted to the desired product by chromic acid oxidation in acetic acid. Similarly known from Chemical Abstracts 87-134,266 h is the preparation of m-CF$_3$SC$_6$H$_4$SO$_2$CF$_3$ by trifluoromethylation with CF$_3$I of the corresponding thiol in liquid ammonia under ultraviolet irradiation.

One skilled in the art would recognize that these processes can only be carried out with great difficulty on an industrial scale, in view of the many stages that are required, the problems in the application of each one of these stages, and the non-accessibility on an industrial scale of some of the reagents involved in these processes. Furthermore, poor yields are obtained.

Trifluoromethylthiophenyl sulfones have been prepared in the prior art by way of Grignard reaction of the corresponding benzonitriles (see, for example, U.S. Pat. No. 3,732,307). The Grignard reaction, of course, makes this process of limited interest on an industrial scale.

Also known in the prior art (Olah, *Friedel-Crafts and Related Reactions* III, Part II, Interscience Publishers, p. 1319 et seq. (1964)) are direct sulfonylation reactions: the reaction of a sulfonic acid, a derivative or a precursor thereof with benzene derivatives in the presence, in particular, of aluminum chloride. Experiments have shown that these processes do not yield any of the desired product if the benzene compound bears a polyhaloalkoxy or polyhaloalkylthio, in particular an OCF$_3$ or SCF$_3$, substituent; the latter are even degraded under the reaction conditions.

The operating conditions have now been determined which make it possible to carry out the sulfonylation reaction on aromatic substrates having a polyhaloalkoxy or polyhaloalkylthio substituent, which could not be achieved according to the prior art.

The instant invention is directed to a process for the preparation of α,α-difluoroalkoxy or α,α-difluoroalkylthiophenyl sulfones, characterized in that a polyhaloalkoxybenzene or a polyhaloalkylthiobenzene is reacted with a sulfonic acid, a derivative or a precursor thereof in the presence of boron trifluoride in an amount such that the absolute pressure of the boron trifluoride within the reaction vessel exceeds 1 bar, and in the presence of hydrofluoric acid as solvent.

The process according to the present invention is of that much more surprising a character inasmuch as it is stated in the prior art (cf. Olah, page 1338, supra) that boron trifluoride is inactive when used as a catalyst in sulfonylation reactions.

Within the scope of this invention, the terms polyhaloalkoxybenzene and polyhaloalkylthiobenzene refer both to the compounds themselves and to analogues thereof with one or a plurality of substituents on the benzene nucleus.

More particularly, the polyhaloalkoxybenzenes or polyhaloalkylthiobenzenes embraced by this invention have the general formula:

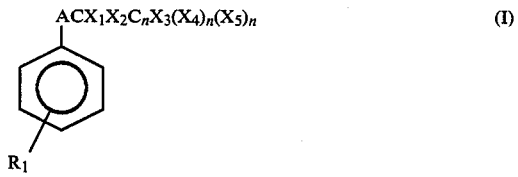

(I)

wherein X$_1$ and X$_2$ are identical or different and represent Cl, Br, I, or F; X$_3$, X$_4$ and X$_5$ are identical or different and represent H, Cl, Br, I or F; n is zero or an integer equal to or less than 5 ($0 \leq n \leq 5$); A represents O or S; and R$_1$ represents at least one element or moiety selected from hydrogen, OH, Cl, Br, I, F, alkyl and alkoxyl radicals having from 1 to 6 carbon atoms, and phenyl and phenoxy radicals substituted by at least one group more deactivating than the ACX$_1$X$_2$C$_n$X$_3$(X$_4$)$_n$(X$_5$)$_n$ group.

The phenyl and phenoxy radicals R$_1$ must be substituted by a group or groups more deactivating than the ACX$_1$X$_2$C$_n$X$_3$(X$_4$)$_n$(X$_5$)$_n$ group so that the acylation reaction takes place on the benzene nucleus carrying the ACX$_1$X$_2$C$_n$X$_3$(X$_4$)$_n$(X$_5$)$_n$ group. Otherwise, acylation would occur on the phenyl or phenoxy radical. Examples of groups more deactivating than the ACX$_1$X$_2$C$_n$X$_3$(X$_4$)$_n$(X$_5$)$_n$ group include COOH, CN, NO$_2$, CX$_1$X$_2$X$_3$ groups and keto groups.

The compounds of Formula I in which n=0 or 1 and X$_1$, X$_2$ and X$_3$ are identical are of particular interest in the present invention. Among these, compounds in which X$_1$, X$_2$ and X$_3$ represent fluorine are preferred.

One can cite as examples of compounds of Formula I the following: trifluoromethoxybenzene; trifluoromethylthiobenzene; o-, m- and p-chlorotrifluoromethoxybenzene; o-, m- and p-chlorotrifluoromethylthiobenzene; o-, m-, and p-bromotrifluoromethylthiobenzene; o-, m- and p-bromotrifluoromethoxybenzene; o-, m- and p-methyltrifluoromethoxybenzene; o-, m- and p-methoxytrifluoromethoxybenzene; o-, m- and p-methoxytrifluoromethylthiobenzene; o-, m- and p-hydroxytrifluoromethoxybenzene; o-, m- and p-hydroxytrifluoromethylthiobenzene; 4-trifluoromethyl-4'-trifluoromethoxybiphenyl; and 3-nitro-4'-trifluoromethoxydiphenyl oxide (as well as the chlorinated, brominated, or iodinated analogues of the above compounds); difluorobromomethoxybenzene; difluorobromomethylthiobenzene; dichlorofluoromethoxybenzene; dichlorofluoromethylthiobenzene; difluorochloromethoxybenzene; difluorochloromethylthiobenzene; α,α,β,β,β-pentachloroethoxybenzene; α,α,β,β,β-pentachloroethylthiobenzene; difluoromethoxybenzene; difluoromethylthiobenzene; α,α,β,β-tetrafluoroethoxybenzene; α,α,ββ-tetrafluoroethylthiobenzene; α,α,β,β-tetrafluoro-β-bromoethoxybenzene; α,α,β,β-tetrafluoro-β-bromoethylthiobenzene; and α,α-difluoro-β,β,β-trichloroethoxybenzene.

Within the scope of this invention, the terms sulfonic acids, precursors and derivatives thereof refer to all the sulfonylation reagents well known in the prior art.

According to a particular embodiment of the invention, the sulfonic acid, its precursor or derivative is of the general formula:

$$R_2SO_2X_6 \quad (II)$$

wherein $R_2$ represents an aliphatic or aromatic radical and $X_6$ represents halogen, OH, $OR_3$, $NH_2$, $NHR_4$ or $NR_5R_6$, wherein each of $R_3$, $R_4$, $R_5$, and $R_6$ is an aromatic or aliphatic radical.

The invention is well suited in particular to the use of a compound of Formula II wherein $R_2$ represents an alkyl, phenyl, alkylphenyl or phenylalkyl radical or a phenyl radical bearing at least one substituent such as, for example, halogen, $NO_2$, CN, $NH_2$ or COOH.

Examples of such compounds include paratoluenesulfonyl chloride, benzenesulfonyl chloride, paratoluenesulfonic acid, benzenesulfonic acid, methanesulfonyl chloride, ethanesulfonyl chloride, orthotoluenesulfonyl chloride, 2,4-dimethylbenzenesulfonyl chloride, metanitrobenzenesulfonyl chloride, 2-methoxybenzenesulfonyl chloride, parachlorobenzenesulfonyl chloride, 3-nitro-4-chlorobenzenesulfonyl chloride, parahydroxybenzenesulfonyl fluoride and parabenzylbenzenesulfonyl chloride.

The process according to the invention is preferably carried out by using an amount of hydrofluoric acid such that the molar ratio of hydrofluoric acid to the compound of Formula I is between 5 and 50. Even more preferably, this ratio is between 10 and 30.

The hydrofluoric acid used is preferably anhydrous. The use of an aqueous hydrofluoric acid would result in a useless consumption of boron trifluoride in the form of a complex of HF, $BF_3$ and $H_2O$ ($H_3O^+BF_4^-$).

The compounds of Formulas I and II are used in substantially equimolar amounts. A slight excess of the compound of Formula I may, however, be desirable.

More particularly, it is preferred to use an amount of boron trifluoride such that the absolute pressure of $BF_3$ within the reaction vessel is between 6 and 20 bars. A pressure in excess of 20 bars is not excluded from the scope of the invention; however, it does not provide any particular benefit. The pressure will therefore be adjusted to maximize the efficiency of the process.

The process according to the invention is preferably carried out at a temperature between $-20°$ and $150°$ C. The reaction times are generally between a few minutes and several hours.

The $\alpha,\alpha$-difluoroalkoxy or $\alpha,\alpha$-difluoroalkylthiophenyl sulfones obtained according to the process of the invention have the general formula:

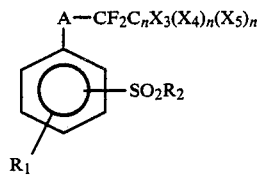

wherein A, $R_1$, $R_2$, $X_3$, $X_4$, $X_5$ and n have the same meaning as above.

Upon completion of the reaction, which is performed in an HF medium, the resultant compound will bear a substituent $ACF_3$ when, in the compound of Formula I, n=0 and $X_3$ is a halogen. The groups $ACCl_3$, $ACBr_3$, $ACI_3$, $ACF_2Br$, $ACCl_2F$, $ACF_2Cl$, etc., are transformed into $ACF_3$. When n=0 and $X_3$ is hydrogen, the resultant compound will bear a substituent $ACF_2H$. When n is greater than zero, only the substituents $X_1$ and $X_2$, when they are not originally fluorine, will be exchanged therefor.

The position of the $SO_2R_2$ group with respect to the $ACF_2C_nX_3(X_4)_n(X_5)_n$ and $R_1$ groups is in conformity with the substitution rules well known to the organic chemist.

The sulfones produced by the process of the invention are useful, in particular, as intermediates in the synthesis of compounds having a pharmaceutical or phytosanitary (e.g., herbicidal) activity.

The following are examples of compounds that can be prepared by the process of the invention: 4-trifluoromethoxydiphenyl sulfone; 4-trifluoromethoxy-4'-methyldiphenyl sulfone; 4-trifluoromethylthio-4'-methyldiphenyl sulfone; 4-nitro-4'-trifluoromethoxydiphenyl sulfone; 4-nitro-4'-trifluoromethylthiodiphenyl sulfone; 4-trifluoromethoxy-4'-chlorodiphenyl sulfone; 4-trifluoromethoxy-2'-methyldiphenyl sulfone; 4-trifluoromethoxy-2-chlorodiphenyl sulfone; 4-trifluoromethylthio-2'-methyldiphenyl sulfone; 4-trifluoromethoxyphenylmethyl sulfone; 4-trifluoromethylthiophenylmethyl sulfone; 4-trifluoromethoxyphenylethyl sulfone; 4-trifluoromethylthio-2',4'-dimethyldiphenyl sulfone; 3-nitro-4'-trifluoromethylthiodiphenyl sulfone; 3-trifluoromethoxy-6-chloro-4'-methyldiphenyl sulfone; 2-trifluoromethoxy-5-chloro-4'-methyldiphenyl sulfone; 4-($\alpha,\alpha,\beta,\beta$-tetrafluoroethylthio)-4'-methyldiphenyl sulfone; 4-($\alpha,\alpha$-difluoro-$\beta,\beta,\beta$-trichloroethoxy)-4'-methyldiphenyl sulfone; and 4-($\alpha,\alpha$-difluoromethoxy)-4'-methyldiphenyl sulfone.

In order to disclose more clearly the nature of the present invention, the following examples illustrating specific embodiments of the invention are given. It should be understood, however, that this is done solely by way of example and is intended neither to delineate the scope of the invention nor limit the ambit of the appended claims.

EXAMPLE 1

Into a 250 ml stainless steel reactor equipped with a magnetic stirrer system, 100 ml of anhydrous HF, 38.1 g (0.2 mole) of p-toluenesulfonyl chloride and 32.4 g (0.2 mole) of trifluoromethoxybenzene were introduced at around 0° C. The reactor was closed and gaseous boron trifluoride ($BF_3$) introduced until the pressure was constant at 10 bars. The reaction was then allowed to proceed with stirring at ambient temperature for 20 hours. Following reaction, the reactor was decompressed to atmospheric pressure and the reaction mixture poured over 200 g of crushed ice. The resultant heterogeneous mixture was extracted three times with 200 ml of methylene chloride. The organic phases were washed three times with 200 ml of water, once with 200 ml of an aqueous 3% potassium hydroxide solution and twice with 200 ml of water. The organic phase was dried over magnesium sulfate and the solvent eliminated by distillation under reduced pressure. 59 g (yield: 94%) of 4-trifluoromethoxy-4'-methyldiphenyl sulfone having a purity of 99.4% was recovered. Melting point: 75.5°–76° C. (MeOH).

EXAMPLE 2

The procedure of Example 1 was followed with the following compounds and under the following conditions:

| | |
|---|---|
| Anhydrous hydrofluoric acid | 100 g |
| Trifluoromethoxybenzene | 32.4 g (0.2 mole) |
| Benzenesulfonyl chloride | 35.2 g (0.2 mole) |
| Boron trifluoride | 10 bars at 20° C. |
| Temperature | 20° C. |
| Duration | 3 hours |

46 g (yield: 76%) of 4-trifluoromethoxydiphenyl sulfone having a purity of 98.5% was recovered. Melting point: 59°–60° C. (MeOH).

EXAMPLE 3

The procedure of Example 1 was followed with the following compounds and under the following conditions:

| | |
|---|---|
| Anhydrous hydrofluoric acid | 100 g |
| Trifluoromethoxybenzene | 32.4 g (0.2 mole) |
| p-toluenesulfonic acid | 34.4 g (0.2 mole) |
| Boron trifluoride | 10 bars at 20° C. |
| Temperature | 30° C. |
| Duration | 4 hours |

45.6 (yield: 72%) of 4-trifluoromethoxy-4'-methyldiphenyl sulfone having a purity of 99% was recovered. Melting point: 75.5°–76° C. (MeOH).

EXAMPLE 4

The procedure of Example 1 was followed with the following compounds and under the following conditions:

| | |
|---|---|
| Anhydrous hydrofluoric acid | 100 g |
| Trifluoromethoxybenzene | 32.4 g (0.2 mole) |
| Methanesulfonyl chloride | 22.9 g (0.2 mole) |
| Boron trifluoride | 10 bars at 20° C. |
| Temperature | 80° C. |
| Duration | 5 hours |

13 g of a mixture comprising 60% 4-trifluoromethoxyphenylmethyl sulfone was recovered.

EXAMPLE 5

The procedure of Example 1 was followed with the following compounds and under the following conditions:

| | |
|---|---|
| Anhydrous hydrofluoric acid | 100 g |
| Trifluoromethylthiobenzene | 17.8 g (0.1 mole) |
| Benzenesulfonyl chloride | 17.6 g (0.1 mole) |
| Boron trifluoride | 10 bars at 20° C. |
| Temperature | 50° C. |
| Duration | 20 hours |

27 g (yield: 85%) of 4-trifluoromethylthiodiphenyl sulfone having a purity of 70% was recovered.

EXAMPLE 6

The procedure of Example 1 was followed with the following compounds and under the following conditions:

| | |
|---|---|
| Anhydrous hydrofluoric acid | 100 g |
| Trichloromethoxybenzene | 42.3 g (0.2 mole) |
| p-toluenesulfonyl chloride | 38.1 g (0.2 mole) |
| Boron trifluoride | 10 bars at 20° C. |
| Temperature | 50° C. |
| Duration | 6 hours |

52 g (yield: 82.8%) of 4-trifluoromethoxy-4'-methyldiphenyl sulfone having a purity of 94% was recovered. During the course of the reaction, an increase in pressure caused by the generation of hydrochloric acid resulting from the Cl-F exchange was observed.

EXAMPLE 7

The procedure of Example 1 was followed with the following compounds and under the following conditions:

| | |
|---|---|
| Anhydrous hydrofluoric acid | 100 g |
| Difluorobromomethoxybenzene | 44.6 g (0.2 mole) |
| p-toluenesulfonyl chloride | 38.1 g (0.2 mole) |
| Boron trifluoride | 8 bars at 20° C. |
| Temperature | 40° C. |
| Duration | 5 hours |

54 g (yield: 86%) of 4-trifluoromethoxy-4'-methyldiphenyl sulfone having a purity of 96% was recovered. During the course of the reaction, an increase in pressure caused by the generation of hydrobromic acid resulting from the Br-F exchange was observed.

EXAMPLE 8

The procedure of Example 1 was followed with the following compounds and under the following conditions:

| | |
|---|---|
| Anhydrous hydrofluoric acid | 100 g |
| p-chlorotrifluoromethoxybenzene | 19.7 g (0.1 mole) |
| p-toluenesulfonyl chloride | 19.05 g (0.1 mole) |
| Boron trifluoride | 10 bars at 20° C. |
| Temperature | 130° C. |
| Duration | 22 hours |

6.3 g (yield: 18%) of a mixture of crude 3-trifluoromethoxy-6-chloro-4'-methyldiphenyl sulfone and 2-trifluoromethoxy-5-chloro-4'-methyldiphenyl sulfone was obtained.

EXAMPLE 9

The procedure of Example 1 was followed with the following compounds and under the following conditions:

| | |
|---|---|
| Anhydrous hydrofluoric acid | 20 g |
| $\alpha,\alpha,\beta,\beta$-tetrafluoroethylthiobenzene | 2 g (0.01 mole) |
| p-toluenesulfonyl chloride | 1.9 g (0.01 mole) |
| Boron trifluoride | 10 bars at 20° C. |
| Temperature | 20° C. |
| Duration | 8 hours |

2.3 g (yield: 66%) of crude 4-($\alpha,\alpha,\beta,\beta$-tetrafluoroethylthio)-4'-methyldiphenyl sulfone was recovered.

EXAMPLE 10

The procedure of Example 1 was followed with the following compounds and under the following conditions:

| | |
|---|---|
| Anhydrous hydrofluoric acid | 40 g |
| α,α,β,β,β-pentachloroethoxybenzene | 5 g (0.017 mole) |
| p-toluenesulfonyl chloride | 3.8 g (0.02 mole) |
| Boron trifluoride | 8 bars at 20° C. |
| Temperature | 30° C. |
| Duration | 5 hours |

3.1 g (yield: 44%) of crude 4-(α,α-difluoro-β,β,β-trichloroethoxy)-4'-methyldiphenyl sulfone was recovered.

EXAMPLE 11

The procedure of Example 1 was followed with the following compounds and under the following conditions:

| | |
|---|---|
| Anhydrous hydrofluoric acid | 100 g |
| α,α-difluoromethoxybenzene | 14.4 g (0.1 mole) |
| p-toluenesulfonyl chloride | 19 g (0.1 mole) |
| Boron trifluoride | 12 bars at 20° C. |
| Temperature | 20° C. |
| Duration | 6 hours |

18.2 g (yield: 61%) of crude 4-(α,α-difluoromethoxy)-4'-methyldiphenyl sulfone was recovered.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed.

I claim:

1. A process for the preparation of α,α-difluoroalkoxy or α,α-difluoroalkylthiophenyl sulfones having the formula:

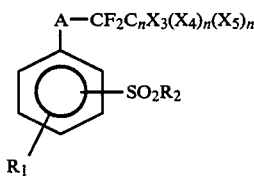

said process comprising reacting a polyhaloalkoxybenzene or a polyhaloalkylthiobenzene having the formula:

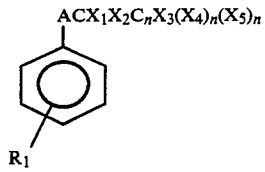

in a reaction vessel with a sulfonic acid, derivative, or precursor thereof having the formula:

$$R_2SO_2X_6 \quad (III)$$

in the presence of boron trifluoride in an amount such that the absolute pressure of the boron trifluoride within the reaction vessel exceeds 1 bar and in the presence of hydrofluoric acid as a solvent; wherein A represents O or S;

$X_1$ and $X_2$ are identical or different and represent Cl, Br, I, or F;

$X_3$, $X_4$, and $X_5$ are identical or different and represent H, Cl, Br, I, or F;

$X_6$ represents halogen, OH, $OR_3$, $NH_2$, $NHR_4$, or $NR_5R_6$, wherein each of $R_3$, $R_4$, $R_5$, and $R_6$ is an aromatic or aliphatic radical;

n is zero or an integer equal to or less than 5 and when n equals zero $X_3$ in formula I is F or H;

$R_1$ represents at least one element or moiety selected from hydrogen, OH, Cl, Br, I, F, alkyl and alkoxy radicals having from 1 to 6 carbon atoms, and phenyl and phenoxy radicals substituted by at least one group more deactivating than the $ACX_1X_2C_nX_3(X_4)_n(X_5)_n$ group; and $R_2$ is a radical selected from the group consisting of alkyl, phenyl, alkylphenyl, phenylalkyl, and phenyl bearing at least one halogen, $NO_2$, CN, $NH_2$, or COOH substituent.

2. A process according to claim 1 wherein n=0 or 1 and $X_1$, $X_2$, and $X_3$ are identical.

3. A process according to claim 2 wherein $X_1$, $X_2$, and $X_3$ represent fluorine.

4. A process according to claim 1 wherein an amount of hydrofluoric acid is used such that the molar ratio of the hydrofluoric acid to the compound of formula II is between 5 and 50.

5. A process according to claim 1 wherein the hydrofluoric acid used is anhydrous hydrofluoric acid.

6. A process according to claim 1 wherein the compounds of formulas II and III are used in substantially equimolar amounts.

7. A process according to claim 1 wherein an amount of boron trifluoride is used such that the absolute pressure of $BF_3$ within the reaction vessel is from 6 to 20 bars.

8. A process according to claim 1 wherein the reaction temperature is from −20° C. to 150° C.

* * * * *